(12) United States Patent
Chung et al.

(10) Patent No.: US 10,047,125 B2
(45) Date of Patent: Aug. 14, 2018

(54) PEPTIDE HAVING ACTIVITY TO IMPROVE SKIN CONDITION AND USE THEREOF

(71) Applicant: CAREGEN CO., LTD., Anyang-si (KR)

(72) Inventors: Yong Ji Chung, Yongin-si (KR); Eun Mi Kim, Yongin-si (KR)

(73) Assignee: CAREGEN CO., LTD., Anyang-si (KR)

(*) Notice: Subject to any disclaimer, the term of this patent is extended or adjusted under 35 U.S.C. 154(b) by 0 days.

(21) Appl. No.: 15/532,232

(22) PCT Filed: Jul. 21, 2015

(86) PCT No.: PCT/KR2015/007554
§ 371 (c)(1),
(2) Date: Jun. 1, 2017

(87) PCT Pub. No.: WO2016/088968
PCT Pub. Date: Jun. 9, 2016

(65) Prior Publication Data
US 2017/0267721 A1 Sep. 21, 2017

(30) Foreign Application Priority Data
Dec. 5, 2014 (KR) .................. 10-2014-0173957

(51) Int. Cl.
*A61K 38/00* (2006.01)
*A61K 38/08* (2006.01)
*C07K 7/06* (2006.01)
*A61Q 19/00* (2006.01)
*A61Q 19/02* (2006.01)

(52) U.S. Cl.
CPC .............. *C07K 7/06* (2013.01); *A61K 38/00* (2013.01)

(58) Field of Classification Search
CPC ........ A61K 38/00; A61K 38/08; A61Q 19/00; A61Q 19/08; A61Q 19/02; C07K 7/06
USPC .............. 514/21.6, 18.8, 18.6; 530/300, 328
See application file for complete search history.

(56) References Cited

U.S. PATENT DOCUMENTS

| | | | |
|---|---|---|---|
| 5,516,891 A | 5/1996 | Siwruk et al. | |
| 5,858,710 A * | 1/1999 | Bandman | C07K 14/8135 435/252.3 |
| 5,958,699 A * | 9/1999 | Bandman | C07K 14/8135 435/6.18 |
| 2005/0266498 A1 | 12/2005 | Okamoto et al. | |
| 2010/0279923 A1* | 11/2010 | Schulte | C07K 14/8135 514/1.4 |
| 2011/0206697 A1 | 8/2011 | Chinnaiyan et al. | |
| 2012/0156150 A1 | 6/2012 | Kim et al. | |
| 2014/0328782 A1 | 11/2014 | Chung et al. | |

FOREIGN PATENT DOCUMENTS

| | | |
|---|---|---|
| JP | 2010-222300 A | 10/2010 |
| JP | 2014-526459 A | 10/2014 |
| KR | 10-2004-0023708 A | 3/2004 |
| KR | 10-2012-0058371 A | 6/2012 |
| KR | 10-2013-0104114 A | 9/2013 |
| KR | 10-1363455 B1 | 2/2014 |
| WO | WO-91/08228 A1 | 6/1991 |
| WO | WO-00/53740 A1 | 9/2000 |
| WO | WO-2006/125827 A1 | 11/2006 |
| WO | WO-2013/113774 A1 | 8/2013 |

OTHER PUBLICATIONS

P20155 from UniProt, pp. 1-10, Integrated into UniProtKB/Swiss-Prot Feb. 1, 1991.*
International Search Report dated Nov. 16, 2015 for International Application No. PCT/KR2015/007554, Chung et al., "Peptide Having Activity to Improve Skin Condition and Use Thereof," filed Jul. 21, 2015 (8 pages).
Dimasi et al., "Characterization of engineered hepatitis C virus NS3 protease inhibitors affinity selected from human pancreatic secretory trypsin inhibitor and minibody repertoires," J Virol. 71(10):7461-9 (1997).
Extended European Search Report dated Nov. 7, 2017 for European Patent Application No. 15864719.8, Chung et al., "Peptide having activity to improve skin condition and use thereof," filed Jul. 21, 2015 (6 pages).
Notice of Allowance dated Mar. 29, 2017 for Korean Patent Application No. 10-2014-0173957, Chung et al., "The peptide having the skin condition improvement activity and use thereof," filed Jul. 21, 2015 (3 pages).
Office Action dated Aug. 1, 2016 for Korean Patent Application No. 10-2014-0173957, Chung et al., "The peptide having the skin condition improvement activity and use thereof," filed Jul. 21, 2015 (11 pages).
Rimphanitchayakit et al., "Structure and function of invertebrate Kazal-type serine proteinase inhibitors," Dev Comp Immunol. 34(4):377-86 (2010).
Office Action dated May 15, 2018 for Japanese Patent Application No. 2017-529667, Chung et al., "Peptide Having Activity to Improve Skin Condition and Use Thereof," filed Jul. 21, 2015 (9 pages).
Olmez et al., Protein-Peptide Interactions Revolutionize Drug Development. *Binding Protein*, Edited by Kotb Abdelmohsen, IntechOpen, pp. 49-72, DOI: 10.5772/48418 (2012).

* cited by examiner

*Primary Examiner* — Julie Ha
(74) *Attorney, Agent, or Firm* — Clark & Elbing LLP; Susan M. Michaud

(57) ABSTRACT

A peptide having activity to improve skin condition is described. The peptide exhibits a very excellent effect in improving skin condition by inhibiting MMP2 activity. A composition containing the peptide exhibits excellent biological activities, such as inhibiting collagen decomposition and melanosome migration, and thus can be used in wrinkle reduction, skin regeneration, skin elasticity improvement, anti-skin aging, wound regeneration, acne reduction, skin regeneration or skin whitening. The composition containing the peptide can be used as a pharmaceutical composition for preventing or treating MMP activity-related diseases and inflammation diseases.

7 Claims, 17 Drawing Sheets

[Fig 2a]
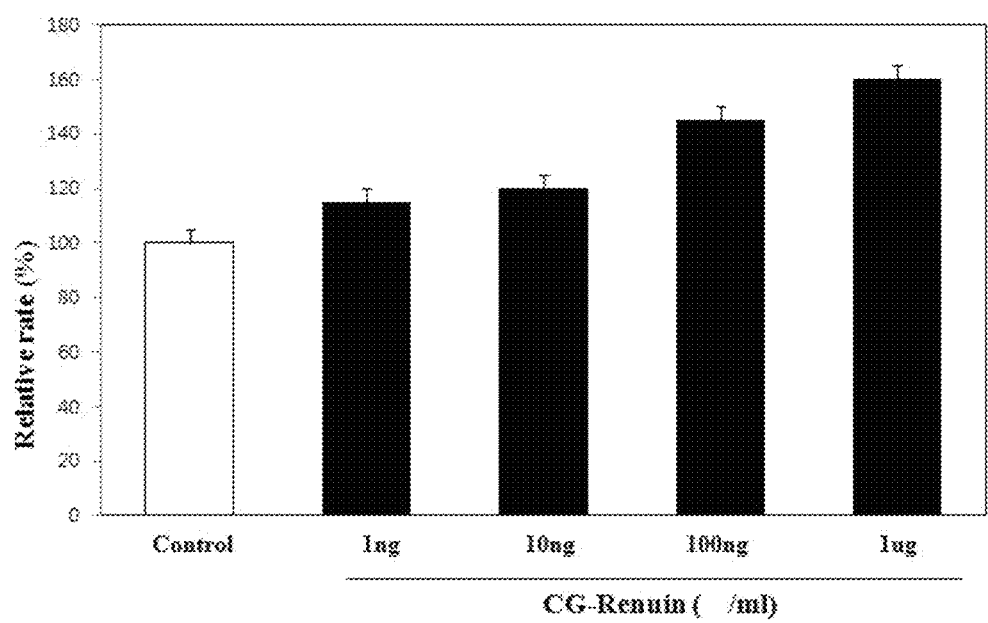

[Fig 2b]
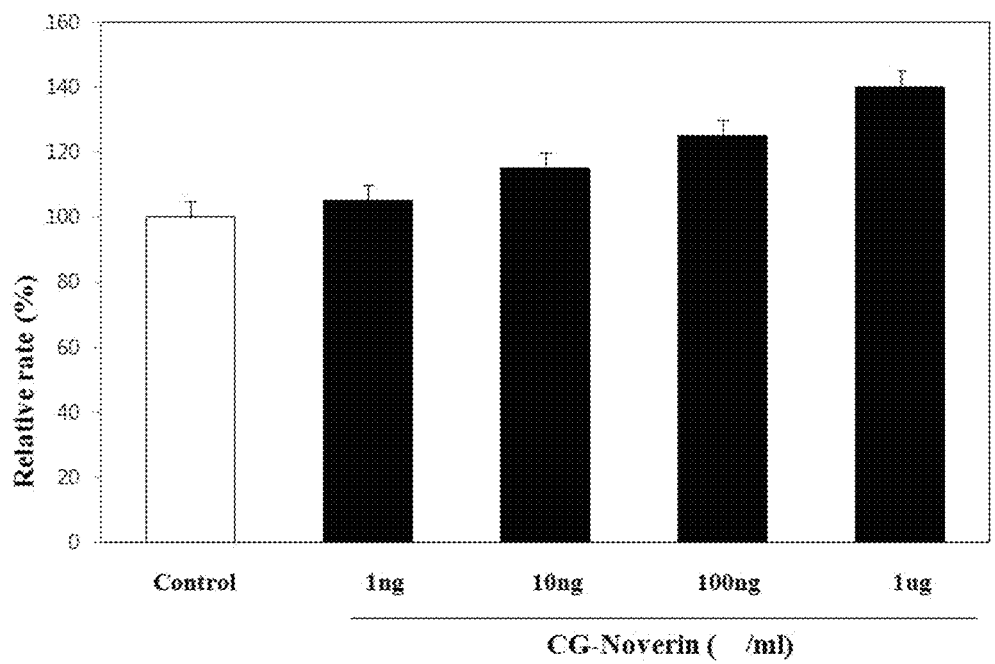

[Fig 3a]
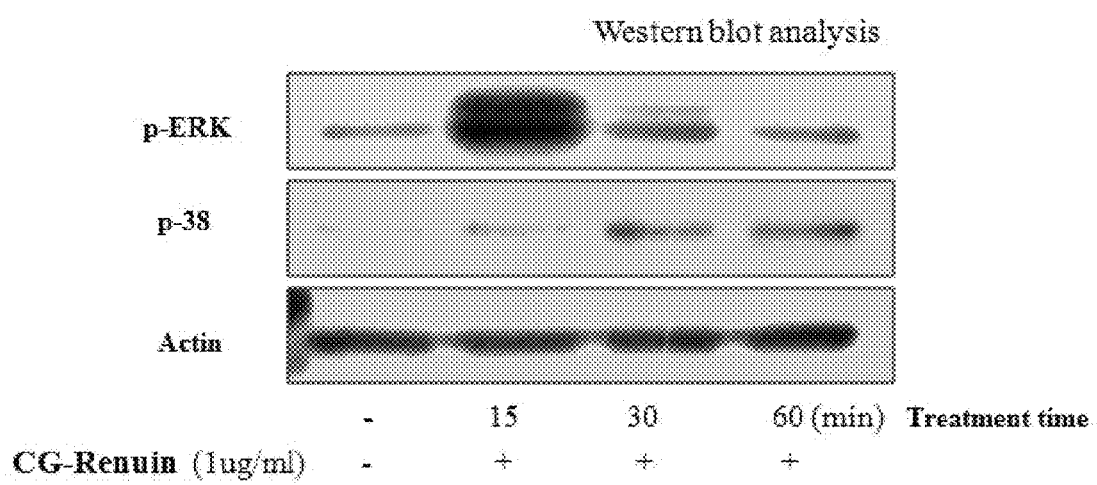

[Fig 3b]
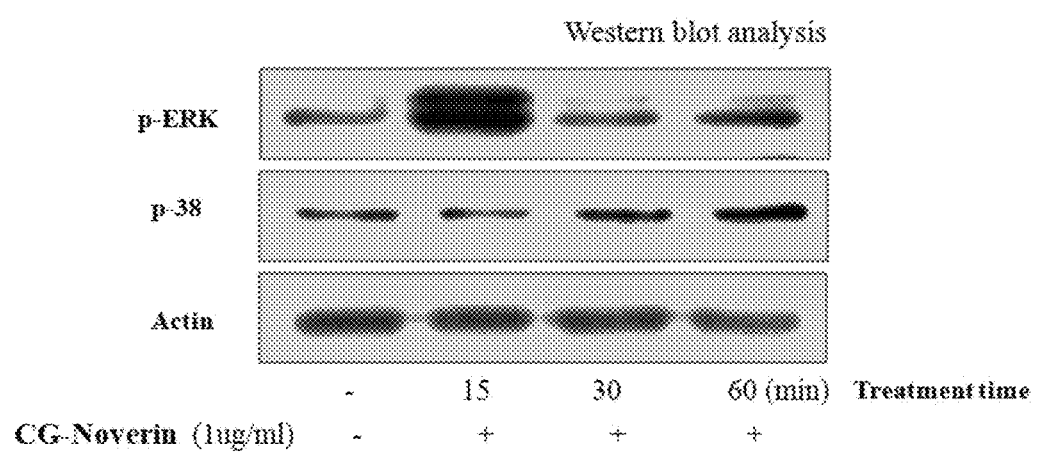

[Fig 4a]
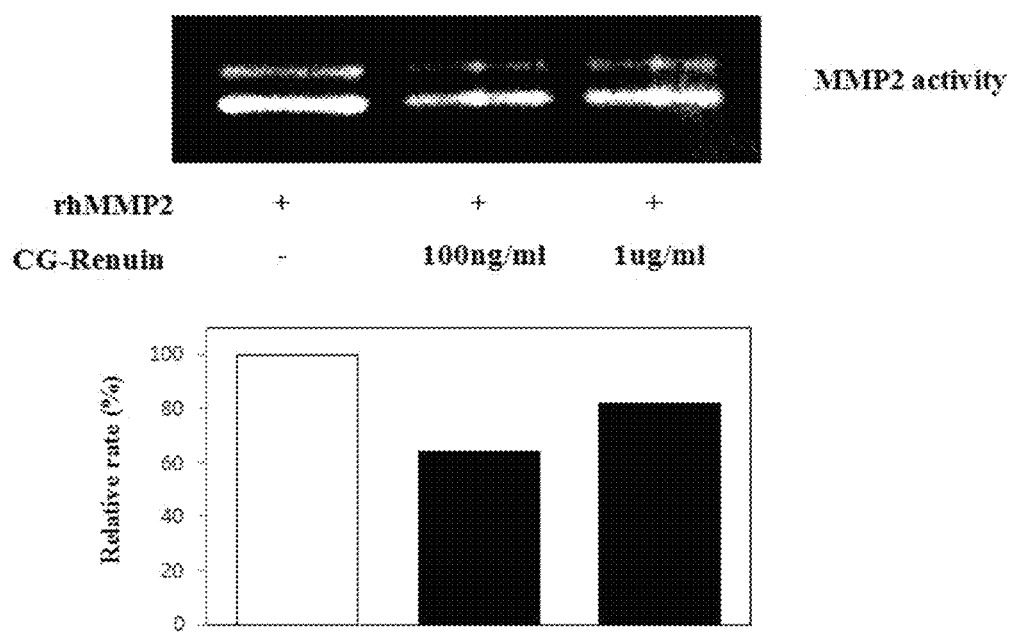

[Fig 4b]
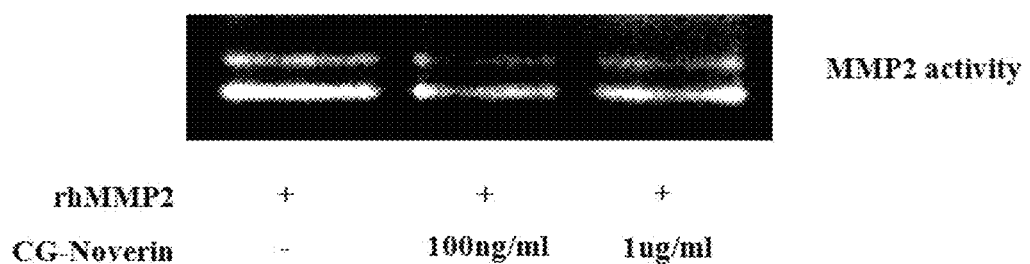

[Fig 5a]
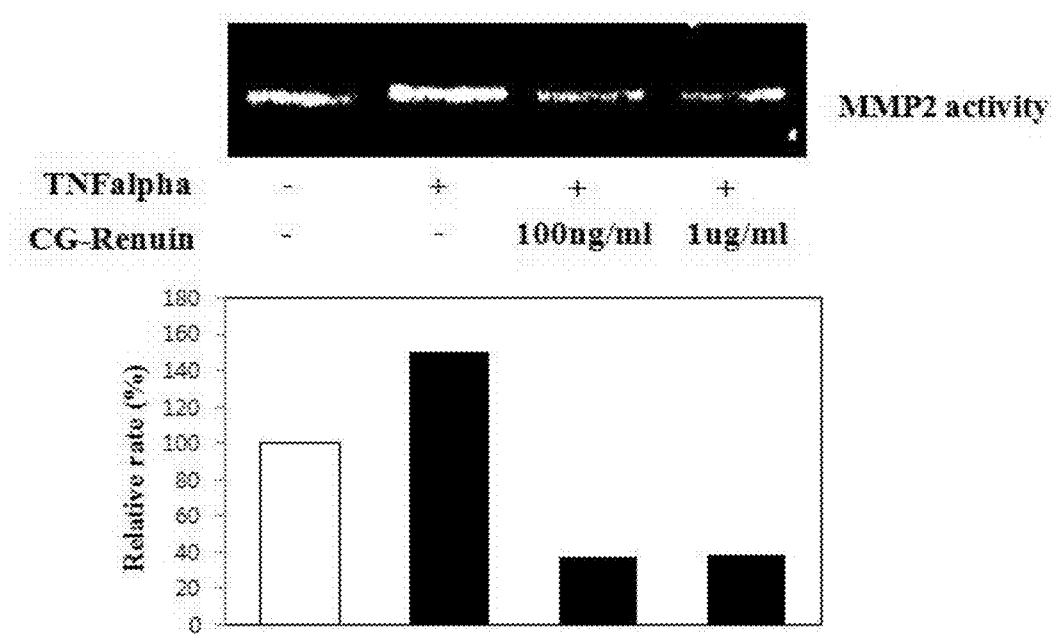

[Fig 5b]
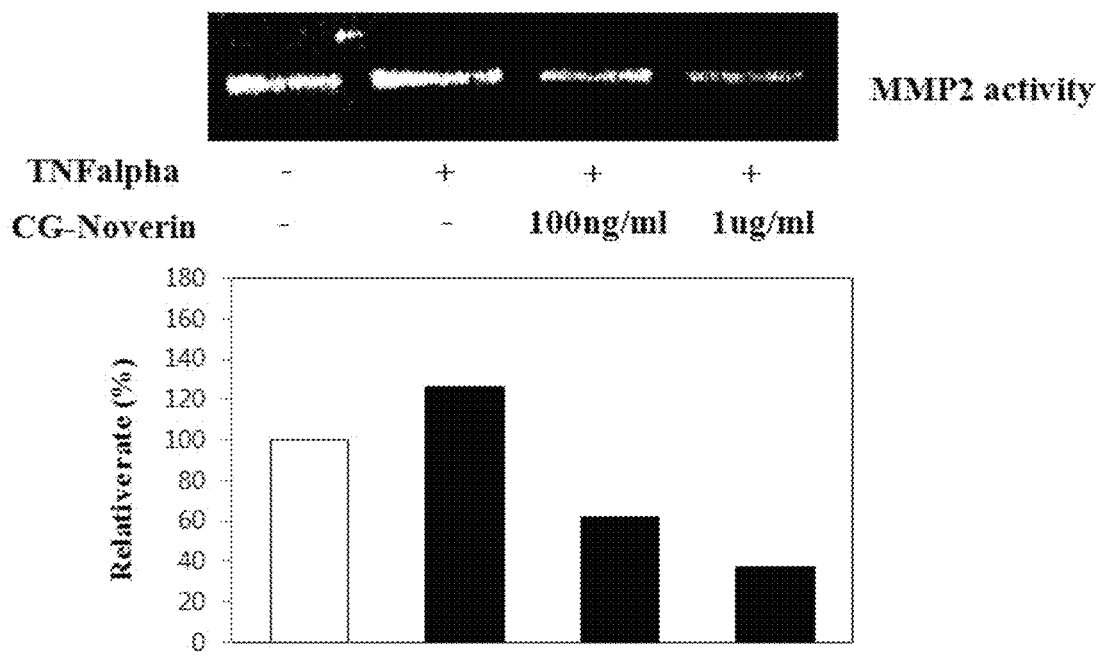

[Fig 6a]
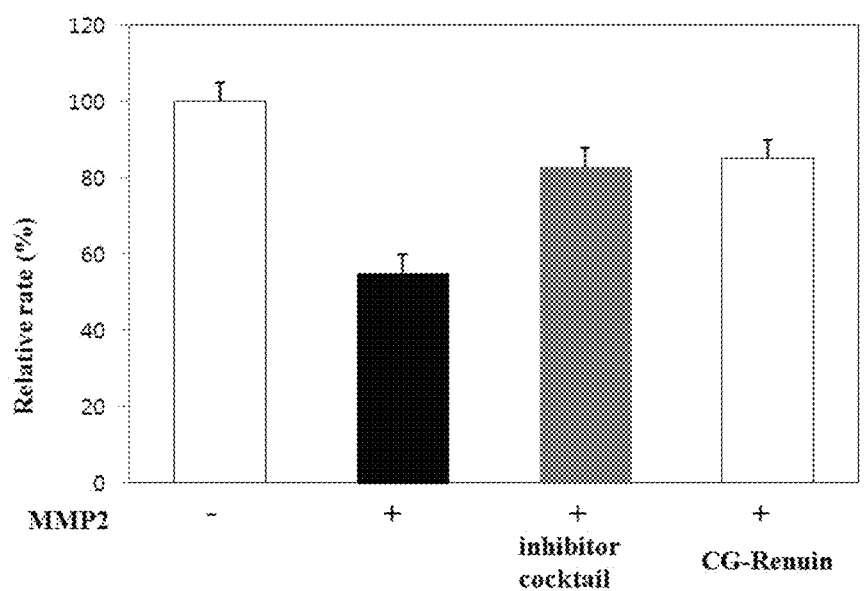

[Fig 6b]
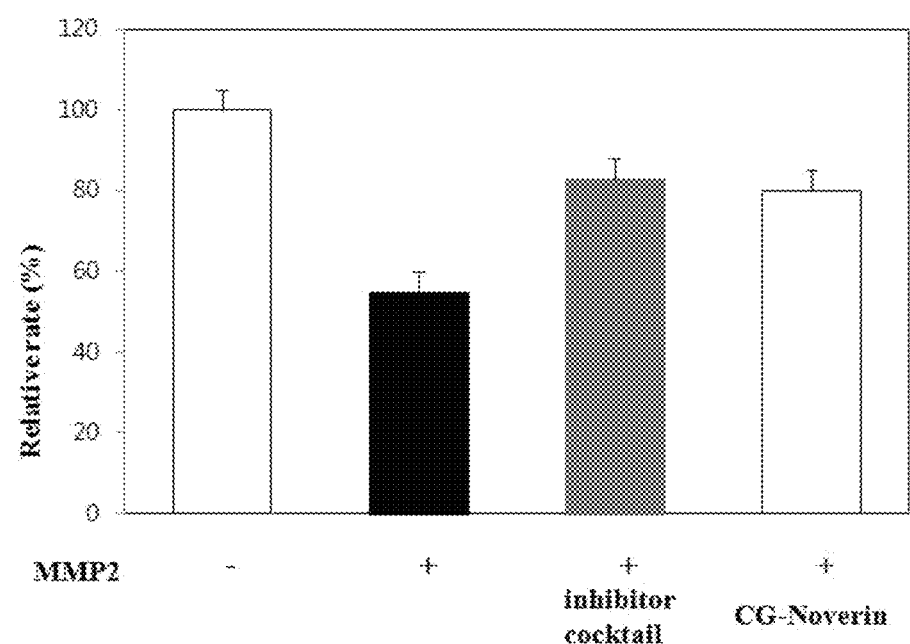

[Fig 7a]
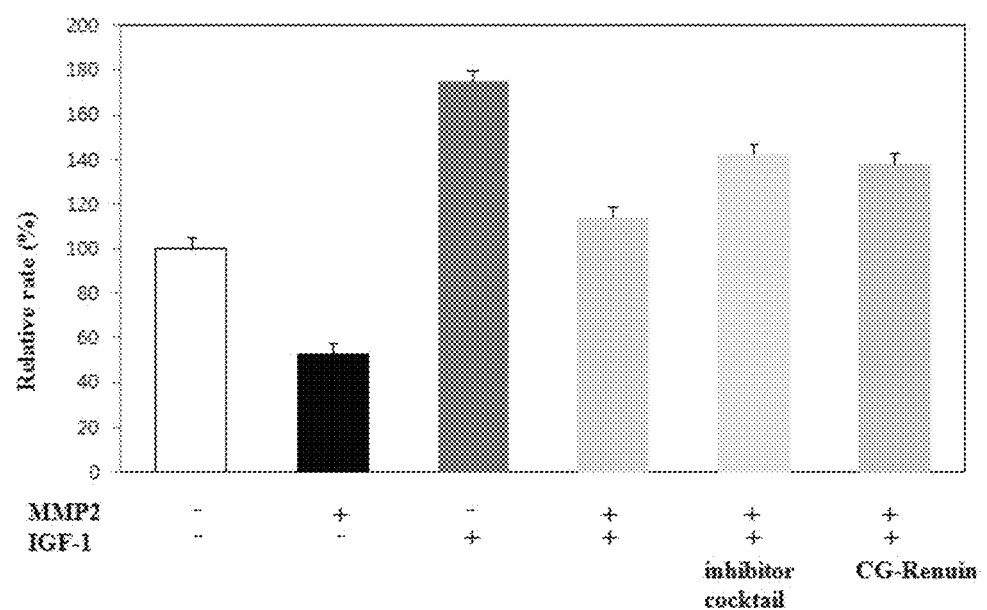

[Fig 7b]
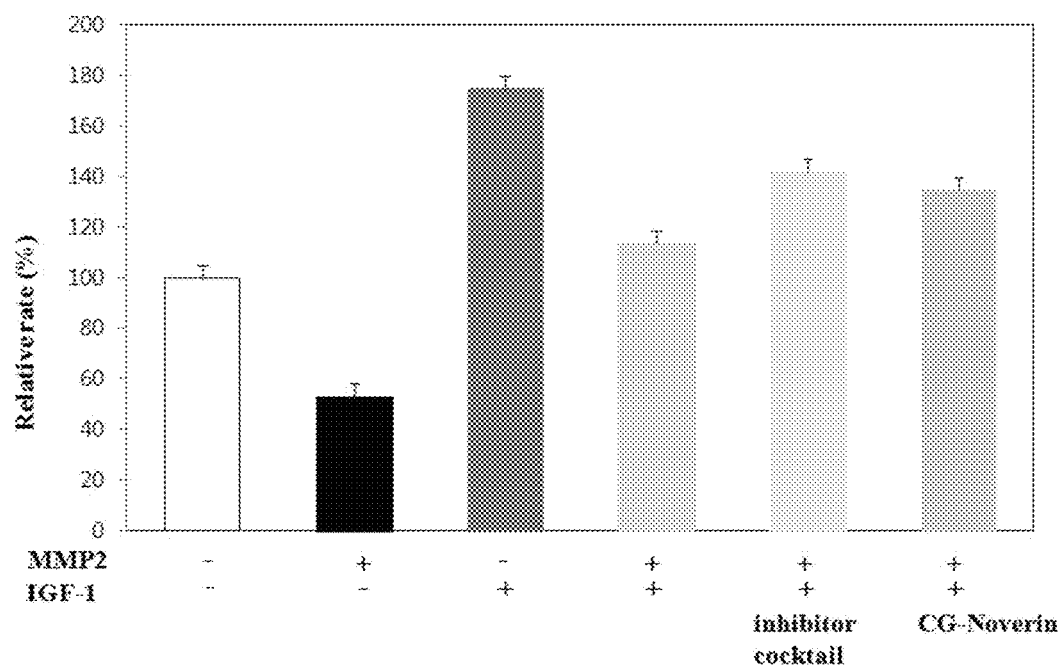

[Fig 8a]
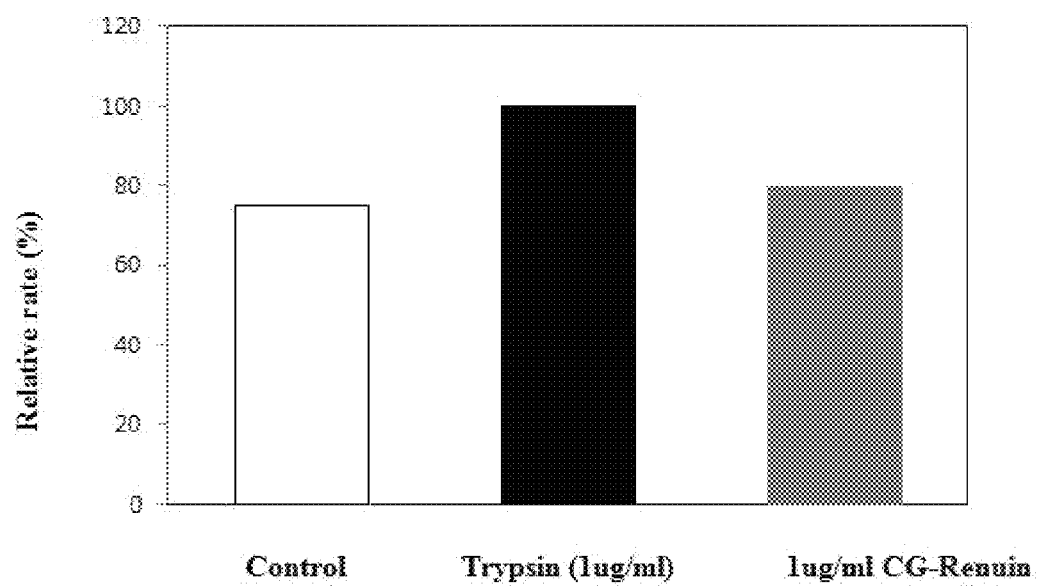

[Fig 8b]
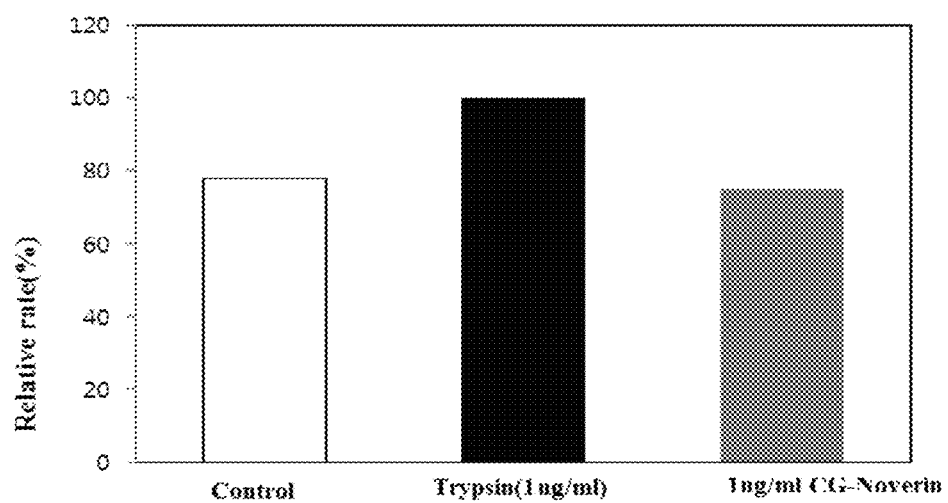

[Fig 9]
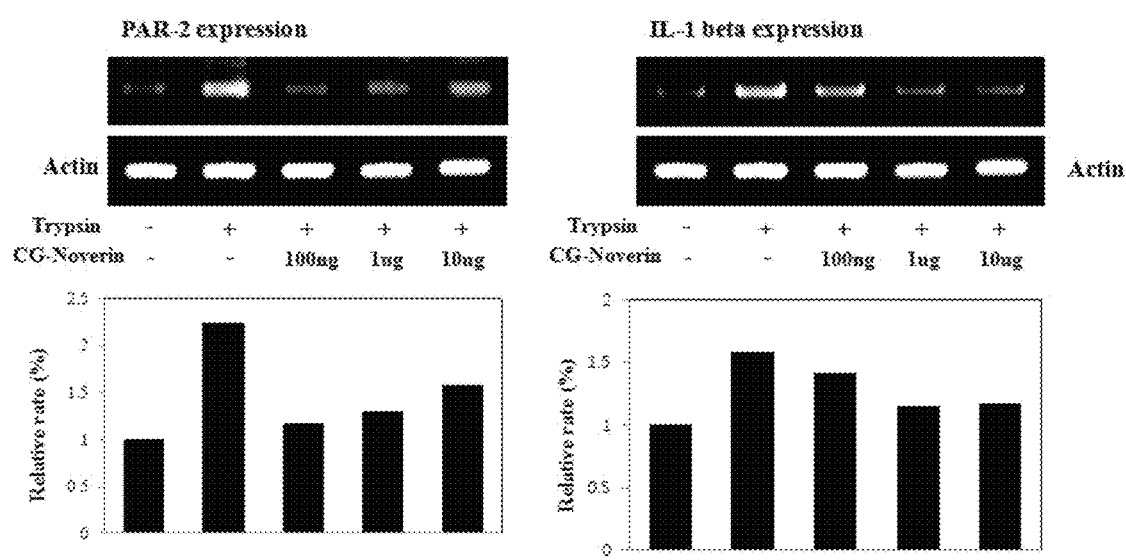

PEPTIDE HAVING ACTIVITY TO IMPROVE SKIN CONDITION AND USE THEREOF

TECHNICAL FIELD

The present invention relates to a peptide having an activity to improve skin condition and a use thereof.

BACKGROUND ART

Matrix metalloproteinases (MMPs) are endopeptidases that can degrade macro biomolecules, such as collagen, proteoglycan and gelatin, and are grouped into collagenases, gelatinases, stromelysins and membrane-type MMPs. All the MMPs are expressed in the form of a pro-enzyme, and a portion of MMP is cleaved so that MMP is activated (Bond, J. S., et al., Int. *J. Biochem.,* 75, 565-574(1985); Chen, J. M., Chen, W. T., *Cell,* 48, 193-203(1987); Harris, E. D. et al., *Coll Rel Res,* 4, 493-512(1984)).

It has been reported that collagenases act on triple-helix form epileptic collagen and gelatin, are grouped into three kinds of collagenases, such as fibroblast collagenase, neutrophil collagenase and collagenase-3, and cleave types I, II and III collagen fibrils (Goldberg, G. I., et al, *J. Biol. Chem.,* 261, 6600-6605(1986); Fini, M. E., et al., *Biochemistry,* 26, 6155-6165(1987)). In addition, it has been known that these three kinds of collagenases have about 50% or more sequence identity with respect to each other (Borkakoti, et al., *Nature Struct. Biol.,* 1, 106-110(1994); *EMBO, J.,* 13, 1263-1269(1994)).

The structure of the MMPs is divided into three domains: a pro-peptide domain, a catalytic domain and a C-terminal domain. After all of the MMPs are generated and secreted in an inactive, latent form, 80 amino acids of the pro-peptide domain from the N-terminal are cleaved, and MMPs are activated through the removal of the cysteine in the PRCGVPD-sequence motif is (Van Wart, H. E. et al., *Proc. Natl. Acad. Sci. USA,* 87, 5578-5582(1990)). It has been known that the activity of the activated MMPs is inhibited by coupling with MMP tissue inhibitor of matrix metalloproteinase (TIMP), which is a natural inhibitor, and this coupling is regulated by the catalytic domain (Murphy, et al., *J. Niol. Chem.,* 267, 9612-9618(1992)). Various types of MMPs have substrate specificity, and are expressed in metabolic processes even in normal cells when extracellular matrixes or other collagen structures need to be degraded. Examples of the disease mediated by MMPs include arteriosclerosis, inflammatory disease of the central nervous system, Alzheimer's disease, skin aging, rheumatoid arthritis, osteoarthritis, corneal ulcers, bone disease, proteinuria, abdominal aneurysm disease, degenerative cartilage loss caused by traumatic joint injury, demyelinating disease of the nervous system, cirrhosis, glomerulopathy, premature rupture of the embryonic membrane, inflammatory bowel disease, periodontal disease, macular degeneration associated with age, diabetic retinopathy, proliferative vitreoretinopathy, retinopathy of prematurity, keratoconus, Sjogren's syndrome, myopia, ocular tumor, corneal transplant rejection, angiogenesis, cancer invasion and metastasis, and the like. Rheumatoid arthritis and osteoarthritis are caused by autoimmune disorder, but as the diseases progress, the extracellular matrix of articular cartilage is destroyed. Stromelysins have been recognized as major enzymes in the arthritis and joint trauma, and have been found to play an important role in the conversion of procollagenase into activated collagenase. Therefore, the progression of arthritis can be prevented by inhibiting MMP activity, and it has been reported that MMPs are derived from penetrating leukocytes, fibroblast cells, or external microorganisms.

In addition, the collagenase secreted from the stimulation of inflammatory mediators and the collagenase secreted from bacteria degrade collagen, which is the matrix of periodontal tissues, causing receding gums, which is gradually advanced to cause periodontal diseases. The activities of fibroblast collagenase and stromelysin isolated from gums causing inflammation were verified, and the correlation between the enzyme level and the observed level of gingivitis was confirmed (Overall, C. M. et al., *J. Periodontal Res.* 22, 81-88(1987)).

MMPs are involved in the pathogenesis of several diseases of the central nerve system (CNS). It is presumed that MMPs destroy myelin or blood-brain barrier (BBB) by allowing inflammatory mononuclear cells to flow into central nerves, and are involved in the accumulation of amyloid beta protein in Alzheimer's disease (Yong, V W, et al., *Trends Neurosci* 21(2), 75-80(1998)). In addition, it has been reported that: the concentration of MMPs is higher in brains of Alzheimer's disease patients rather than normal brains (Leake A, Morris C M, & Whateley *J. Neurosci Lett* 291(3), 201-3(2000); the level of gelatinase B in the cerebrospinal fluid is associated with multiple sclerosis and other neurological diseases (Miyazaki, K, et al., *Nature* 362, 839~841 (1993)); and MMPs also contribute to the degradation and accumulation of amyloid beta protein (Backstrom J R, et al., *J neurosci* 16(24), 7910-9(1996)).

Since MMPs induce skin aging, the relief and prevention of wrinkles can be expected through the inhibition of MMPs, and MMPs promote angiogenesis and cancer invasion and metastasis through the degradation of basement membranes. Therefore, MMPs play a very important role in cancer invasion and metastasis through the degradation of basement membranes and also mediate various diseases, and thus the development of medicines capable of inhibiting MMPs is required. However, these inhibitors can be used as ideal therapeutics when the inhibitors can be safely used during a long period of time, so that the development of less toxic preparations as MMP activity inhibitors is required. For effective treatment of various diseases mediated by MMPs, MMP inhibitors are being actively studied, and the development of MMP inhibitors is effectively employed for the treatment of various diseases.

Throughout the entire specification, many papers and patent documents are referenced and their citations are represented. The disclosure of the cited papers and patent documents are entirely incorporated by reference into the present specification, and the level of the technical field within which the present invention falls and the details of the present invention are explained more clearly.

DETAILED DESCRIPTION OF THE INVENTION

Technical Problem

The present inventors endeavored to develop excellent peptides having a biologically effective activity, and as a result, the present inventors established that a peptide having an amino acid sequence of SEQ ID NO: 1 or SEQ ID NO: 2 exhibits an MMP2 inhibitory activity and a collagen degradation inhibitory activity and can be favorably used in the improvement of skin condition, and thus, completed the present invention.

Therefore, an aspect of the present invention is to provide a peptide having an activity to improve skin condition.

Another aspect of the present invention is to provide a composition for improving skin condition.

Still another aspect of the present invention is to provide a pharmaceutical composition for preventing or treating an MMP activity-related disease.

Still another aspect of the present invention is to provide a pharmaceutical composition for preventing or treating an inflammatory disease.

Still another aspect of the present invention is to provide a method for improving skin condition.

Still another aspect of the present invention is to provide a method for preventing or treating an inflammation disease.

Other purposes and advantages of the present invention will become more obvious with the following detailed description of the invention, claims and drawings.

Technical Solution

In accordance with an aspect of the present invention, there is provided a peptide having an activity to improve skin condition, the peptide including an amino acid sequence of SEQ ID NO: 1 or SEQ ID NO: 2.

The present inventors endeavored to develop excellent peptides having a biologically effective activity, and as a result, the present inventors established that a peptide having an amino acid sequence of SEQ ID NO: 1 or SEQ ID NO: 2 exhibits an MMP2 inhibitory activity and a collagen degradation inhibitory activity and can be favorably used in the improvement of skin condition.

According to the present invention, the peptide of the present invention includes an amino acid sequence of SEQ ID NO:1 or SEQ ID NO: 2. Specifically, the peptide of the present invention consists essentially of an amino acid sequence of SEQ ID NO: 1 or SEQ ID NO: 2.

As used herein, the term "peptide" refers to a linear molecule in which amino acid residues bind to each other via a peptide linkage. The peptide of the present invention may be prepared by chemical synthesis methods known in the art, especially, solid-phase synthesis techniques (Merrifield, J. Amer. Chem. Soc. 85:2149-54(1963); Stewart, et al., Solid Phase Peptide Synthesis, 2nd. ed., Pierce Chem. Co.: Rockford, 111(1984)) or liquid-phase synthesis techniques (U.S. Pat. No. 5,516,891).

The peptide of the present invention may induce a modification at the N-terminal or C-terminal thereof in order to select some domains of an amino acid sequence and increase the activity thereof. Through such a modification, the peptide of the present invention may have a high half-life resulting from the increased half-life at the in vivo administration thereof.

In addition, the C-terminal of the peptide of the present invention may be modified by a hydroxyl group (—OH), an amino group (—NH$_2$), an azide group (—NHNH$_2$), or the like, and a protecting group selected from the group consisting of an acetyl group, a fluorenyl methoxy carbonyl group, a formyl group, a palmitoyl group, a myristyl group, a stearyl group and polyethylene glycol (PEG) may be linked to the N-terminal of the peptide.

The foregoing amino acid modification significantly improves the stability of the peptide of the present invention. As used herein, the term "stability" refers to storage stability (e.g., room-temperature storage stability) as well as in vivo stability. The foregoing protecting group protects the peptide of the present invention from the attack of in vivo protein cleavage enzymes.

According to an embodiment of the present invention, the peptide of the present invention has not only a function of directly inhibiting the activity of matrix metalloproteinase-2 (MMP2) but also a function of inhibiting the degradation of collagen by MMP2. In addition, the peptide of the present invention has an excellent effect of inhibiting the melanosome transfer involved in skin whitening. These results indicate that the peptide of the present invention has a very excellent effect in the improvement of skin condition.

According to another embodiment of the present invention, there is provided a cosmetic composition for improving skin condition, containing the peptide of the present invention as an active ingredient.

Since the composition of the present invention contains the foregoing peptide of the present invention as an active ingredient, the descriptions of overlapping contents therebetween will be omitted to avoid excessive complexity of the present specification.

According to an embodiment of the present invention, the improving of the skin condition is wrinkle relief, skin elasticity improvement, skin aging inhibition, skin moisture improvement, wound removal, acne relief, skin regeneration, or skin whitening.

The peptide of the present invention has a much smaller molecular weight than other proteins, and thus has a very excellent skin penetration rate. Therefore, the composition of the present invention can effectively improve skin condition when locally applied onto the skin.

According to an embodiment of the present invention, the composition of the present invention is a cosmetic composition containing: (a) a cosmetically effective amount of the foregoing peptide of the present invention; and (b) a cosmetically acceptable carrier.

As used herein, the term "cosmetically effective amount" refers to an amount that is sufficient to attain the efficacy of the composition of the present invention described above.

The cosmetic composition of the present invention may be formulated into any dosage form that is conventionally prepared, and examples thereof may include a solution, a suspension, an emulsion, a paste, a gel, a cream, a lotion, a powder, a soap, a surfactant-containing cleansing, an oil, a powder foundation, an emulsion foundation, a wax foundation and a spray, but are not limited thereto. More specifically, the cosmetic composition of the present invention may be prepared in a dosage form of emollient lotion, nourishing lotion, nourishing cream, massage cream, essence, eye cream, cleansing cream, cleansing foam, cleansing water, pack, spray or powder.

In cases where the dosage form of the present invention is a paste, a cream, or a gel, an animal fiber, a vegetable fiber, wax, paraffin, starch, tragacanth, a cellulose derivative, polyethylene glycol, silicone, bentonite, silica, talc or zinc oxide may be used as a carrier ingredient.

In cases where the dosage form of the present invention is a powder or a spray, lactose, talc, silica, aluminum hydroxide, calcium silicate, or a polyamide powder may be used as the carrier ingredient. Especially, in cases where the dosage form of the present invention is a spray, the spray may further include a propellant, such as chlorofluorohydrocarbon, propane/butane or dimethyl ether.

In cases where the dosage form of the present invention is a solution or an emulsion, a solvent, a solubilizer, or an emulsifier may be used as the carrier ingredient, and examples of the carrier may include water, ethanol, isopropanol, ethyl carbonate, ethyl acetate, benzyl alcohol, benzyl benzoate, propylene glycol, 1,3-butyl glycol oil, glycerol fatty esters, polyethylene glycol and fatty acid esters of sorbitan.

In cases where the dosage form of the present invention is a suspension, liquid diluents (such as water, ethanol and propylene glycol), suspending agents (such as ethoxylated isostearyl alcohol, polyoxyethylene sorbitol ester and polyoxyethylene sorbitan ester), microcrystalline cellulose, aluminum metahydroxide, bentonite, agar, or tragacanth may be used as a carrier ingredient.

In cases where the dosage form of the present invention is a surfactant-containing cleansing, aliphatic alcohol sulfate, aliphatic alcohol ether sulfate, sulfosuccinate monoester, isethionate, imidazolium derivatives, methyl taurate, sarcosinate, fatty acid amide ether sulfate, alkyl amido betaine, aliphatic alcohol, fatty acid glyceride, fatty acid diethanolamide, plant oil, lanoline derivatives, or ethoxylated glycerol fatty acid ester may be used as a carrier ingredient.

The components contained in the cosmetic composition of the present invention include compositions that are commonly used in the cosmetic composition, in addition to the peptides, as active ingredients, and the carrier component thereof, for example, may include common aids, such as an antioxidant, a stabilizer, a solubilizer, vitamins, a pigment and a flavor.

In accordance with another aspect of the present invention, there is provided a pharmaceutical composition for preventing or treating an MMP activity-related disease, the composition containing the peptide of the present invention, wherein the MMP activity-related disease is arthritis, diabetic retinopathy, hypertrophic scarring, psoriasis, ulcers of mucosal and epithelial tissues, inflammation by autoimmunity, lupus as a disease associated with degradation of basement membranes, autoimmune neuropathy, destruction of myocytes, glaucoma, or extra angiogenesis.

The peptides of the present invention exhibit various biological activities, such as inhibiting MMP2 activity, inhibiting collagen degradation and inhibiting melanosome transfer, and thus can be favorably used in the treatment of related diseases.

According to a preferable embodiment of the present invention, the composition of the present invention is a pharmaceutical composition containing: (a) a pharmaceutically effective amount of the above-described peptide of the present invention; and (b) a pharmaceutically acceptable carrier.

As used herein, the term "pharmaceutically effective amount" refers to an amount sufficient to attain efficacy or activity of the foregoing peptide.

The pharmaceutically acceptable carrier contained in the pharmaceutical composition of the present invention is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate and mineral oil. The pharmaceutical composition of the present invention may further contain, in addition to the above ingredients, a lubricant, a wetting agent, a sweetening agent, a flavoring agent, an emulsifier, a suspending agent, a preservative and the like. Suitable pharmaceutically acceptable carriers and agents are described in detail in *Remington's Pharmaceutical Sciences* (19th ed., 1995).

The pharmaceutical composition of the present invention may be administered orally or parenterally, and preferably parenterally. Examples of the parenteral administration may include intramuscular, intravenous, subcutaneous, intraperitoneal, local and transdermal injections.

A suitable dose of the pharmaceutical composition of the present invention may vary depending on various factors, such as the method for formulation, the manner of administration, the age, body weight, gender, morbidity of the patient, the diet, the time of administration, the route of administration, the excretion rate, and response sensitivity. Meanwhile, the preferable dose of the pharmaceutical composition of the present invention is 0.0001-1000 μg per day.

The pharmaceutical composition of the present invention may be formulated into a unit dosage form or may be prepared in a multi-dose container by using a pharmaceutically acceptable carrier and/or excipient according to the method easily conducted by a person having an ordinary skill in the art to which the present invention pertains. Here, the dosage form may be a solution in an oily or aqueous medium, a suspension, an emulsion, an extract, a powder, granules, a tablet or a capsule, and may further contain a dispersant or a stabilizer.

In accordance with still another aspect of the present invention, there is provided a pharmaceutical composition for preventing or treating an inflammatory disease, the composition containing the peptide of the present invention.

According to an embodiment of the present invention, the inflammatory disease, to which the composition of the present invention can be applied, is periodontitis, asthma, eczema, psoriasis, allergy, rheumatoid arthritis, psoriatic arthritis, atopic dermatitis, acne, atopic rhinitis (hay fever), allergic dermatitis (eczema), chronic sinusitis, or seborrheic dermatitis.

The peptides of the present invention inhibits the expressions of protease-activated receptor 2 (PAR2) and IL-1β, which are pro-inflammatory cytokines involve in an inflammation response, thereby reducing the inflammation response, and thus can be favorably used in the prevention and treatment of related diseases.

In accordance with another aspect of the present invention, there is provided a method for improving skin condition, the method including administering, to a subject, the peptide of the present invention.

In accordance with another aspect of the present invention, there is provided a method for preventing or treating an inflammatory diseases, the method including administering, to a subject, the peptide of the present invention.

Advantageous Effects

Features and advantages of the present invention are summarized as follows:

(a) The present invention provides a peptide having an activity to improve skin condition.

(b) The peptide of the present invention exerts a very excellent effect in inhibiting MMP2 activity to improve skin condition; and the composition containing the peptide of the present invention exhibits an excellent biological activity, such as inhibiting collagen degradation and inhibiting melanosome transfer, and thus can be used for wrinkle relief, skin regeneration, skin elasticity improvement, skin aging inhibition, wound tissue regeneration, acne relief, skin regeneration, or skin whitening.

(c) The composition containing the peptide of the present invention can be used as a pharmaceutical composition for preventing or treating MMP activity-related diseases and inflammation diseases.

BRIEF DESCRIPTION OF THE DRAWINGS

FIG. 2 illustrates the results of evaluating human primary dermal fibroblast cell proliferation promoting effects by the peptides of the present invention.
(a) CG-Renuin and (b) CG-Noverin
FIG. 3 illustrates the results of verifying the change in signaling by the peptides of the present invention in human primary dermal fibroblast cells.
(a) CG-Renuin and (b) CG-Noverin
FIG. 4 illustrates the results of evaluating MMP2 activity inhibitory effects by the peptides of the present invention.
(a) CG-Renuin and (b) CG-Noverin
FIG. 5 illustrates the results of evaluating MMP2 activity inhibitory effects by the peptides of the present invention in fibroblast cells.
(a) CG-Renuin and (b) CG-Noverin
FIGS. 6 and 7 illustrate the results of evaluating collagen degradation inhibitory effects by the peptides of the present invention.
(a) CG-Renuin and (b) CG-Noverin
FIG. 8 illustrates the results of evaluating melanosome transfer inhibitory effect by CG-Renuin.

FIG. 9 illustrates the results of evaluating anti-inflammatory effect by CG-Noverin in dental pulp stem cells.

MODE FOR CARRYING OUT THE INVENTION

Figure 1A:
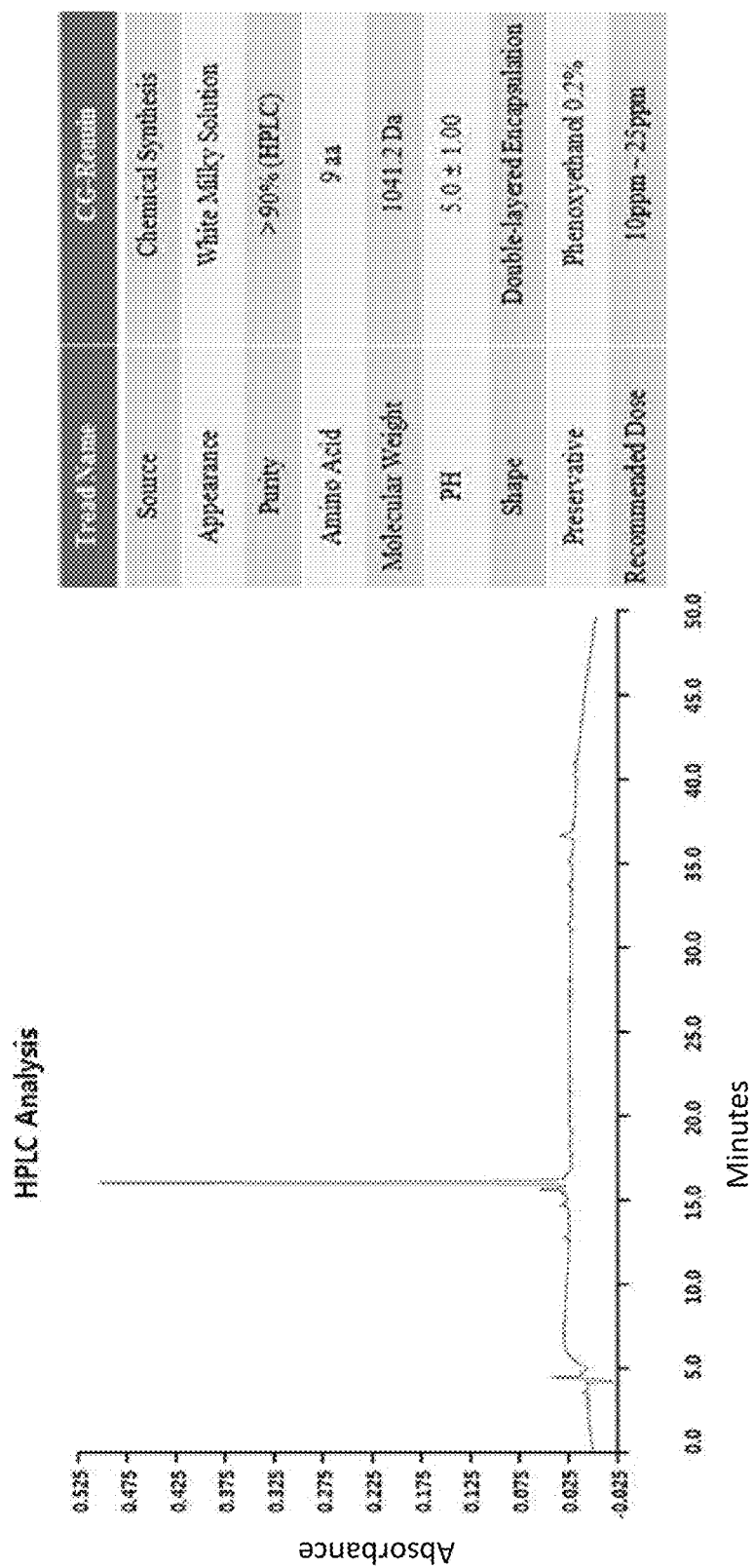
FIG. 1 illustrates HPLC analysis results of the peptides of the present invention.
(a) CG-Renuin and (b) CG-Noverin
Figure 1B:
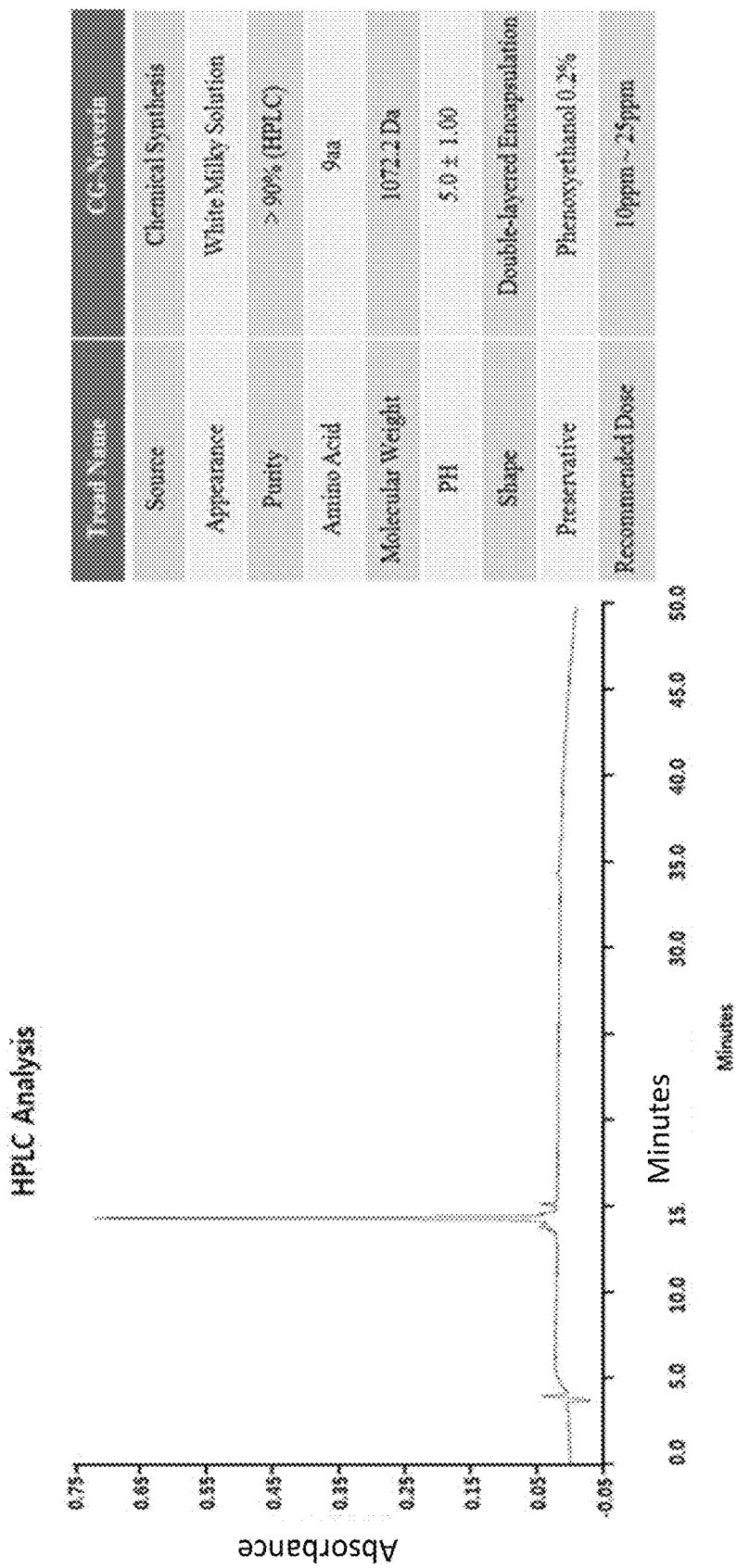

Hereinafter, the present invention will be described in detail with reference to examples. These examples are only for illustrating the present invention more specifically, and it will be apparent to those skilled in the art that the scope of the present invention is not limited by these examples.

EXAMPLES

Synthesis Example 1: Peptide Synthesis 700 mg of chloro trityl chloride resin (CTL resin, Nova Biochem Cat No. 01-64-0021) was put into a reaction container, and 10 ml of methylene chloride (MC) was added, followed by stirring for 3 minutes. After the solution was removed, 10 ml of dimethylform amide (DMF) was added, followed by stirring for 3 minutes, and then the solvent was again removed. 10 ml of a dichloromethane solution was put into the reactor, and 200 mmole Fmoc-Gly-OH (Bachem, Swiss) and 400 mmole diisopropyl ethylamine (DIEA) were added. The mixture was well dissolved with stirring, and the reaction was conducted with stirring for 1 hour. After the reaction, the resultant material was washed, and methanol and DIEA (2:1) were dissolved in DCM, followed by reaction for 10 minutes, and then the resultant material was washed with excessive DCM/DMF (1:1). After the solution was removed, 10 ml of dimethylform amide (DMF) was added, followed by stirring for 3 minutes, and then the solvent was again removed. 10 ml of a deprotection solution (20% piperidine/DMF) was put into the reactor, followed by stirring at room temperature for 10 minutes, and then the solution was removed. An equal amount of a deprotection solution was added, and then the reaction was again maintained for 10 minutes, followed by removal of the solution. The resultant material was washed twice with DMF, once with MC, and once with DMF, for 3 minutes each, thereby preparing Gly-CTL resin. 10 ml of a DMF solution was put in a new reactor, and 200 mmol Fmoc-Cys (Bachem, Swiss), 200 mmol HoBt, and 200 mmole Bop were added, and the mixture was dissolved well with stirring. 400 mmole DIEA was divisionally added twice into the reactor, and then stirring was conducted for at least 5 minutes until all solids were dissolved. The dissolved amino acid mixed solution was put in the reactor containing the deprotected resin, and the reaction was conducted with stirring at room temperature for 1 hour. After the reaction liquid was removed, the stirring was conducted using a DMF solution three times for 5 minutes each, followed by removal. A small amount of the reaction resin was taken to check the degree of reaction by Kaiser test (Ninhydrin test). Using the deprotection solution, the deprotection reaction was conducted twice in the same manner as described above, to prepare Cys-Gly-CTL resin. After sufficient washing with DMF and MC, the Kaiser test was again conducted, and then the following amino acid attachment test was conducted in the same manner as described above. Based on the selected amino acid sequence, a chain reaction was conducted in the order of Fmoc-Ile, Fmoc-Trp, Fmoc-Lys(Boc), Fmoc-Glu(OtBu), Fmoc-Ser(tBu), Fmoc-Ser(tBu), and Fmoc-Glu(OtBu). The Fmoc-protecting group was removed by reaction twice with a deprotection solution for 10 minutes for each, followed by well washing. Acetic anhydride, DIEA, and HoBt were added to perform acetylation for 1 hour, and then the prepared peptidyl resin was washed three times with DMF, MC, and methanol, dried under the flow of nitrogen gas, and completely dried by vacuum-drying under $P_2O_5$. 30 ml of a missing solution (81.5% trifluoroacetic acid (TFA), 5% distilled water, 5% thioanisole, 5% phenol, 2.5% EDT, and 1% TIS] was added, and the reaction was maintained for 2 hours while the mixture was intermittently stirred at room temperature. The resin was obtained through filtration, and the resin was washed with a small amount of a TFA solution, and then mixed with stock solution. The distillation was conducted under reduced pressure to reduce the total volume by half, and then 50 ml of cold ether was added to induce precipitation. Thereafter, the precipitates were collected by centrifugation, followed by washing twice with cold ether. The stock solution was removed, followed by sufficient drying under nitrogen atmosphere, thereby synthesizing 0.5 g of unpurified the NH2-Cys-Thr-Lys-Ile-Tyr-Asp-Pro-Val-Cys-COOH peptide of SEQ ID NO: 1 (yield: 95%), and 0.7 g of the $NH_2$-Cys-Pro-Arg-His-Phe-Asn-Pro-Val-Cys-COOH peptide of SEQ ID NO: 2 (yield: 95%). From the measurement using a molecular weight analysis system, the molecular weights of peptide 1 and peptide 2 were determined as 1041.2 (theoretical value: 1041.25) and 1072.2 (theoretical value: 1072.27), respectively.

TABLE 1

| Peptide | Amino acid sequence | Analysis value (Mass spectrometer) | |
|---|---|---|---|
| | | Analytical value | Theoretical value |
| Sequence 1 | CTKIYDPVC | 1041.2 | 1042.25 |
| Sequence 2 | CPRHFNPVC | 1072.2 | 1072.27 |

Example 1: Promotion of Human Dermal Fibroblast Cell Growth

Human primary dermal fibroblast cells were treated with CG-Renuin (peptide of SEQ ID NO: 1) and CG-Noverin (peptide of SEQ ID NO: 2) at different concentrations (1 ng/ml to 1 ug/ml), and the cells were incubated for 72 hours in a cell incubator. Then, the cell proliferation change by the peptide treatment was analyzed through SRB assay (OD 590 nm). The proliferation of human primary dermal fibroblast cells was increased depending on the treatment amount of CG-Renuin or CG-Noverin (FIGS. 2a and 2b).

Example 2: Signaling of CG-Renuin or CG-Noverin in Human Dermal Fibroblast Cells NIH3T3 cells (epidermal cell line) were seeded in a 6-well plate at a cell density of $2\times10^5$ cells/well, followed by incubation overnight, and then the cells were treated with CG-Renuin or CG-Noverin peptides at different concentrations (1-10 ug/ml), followed by incubation at 37☐ for 30 minutes. Then, the cells were irradiated with UVA (8 J), followed by incubation for 24 hours. The lysates were obtained by the treatment with the cell lysis buffer, followed by protein quantification. For the confirmation of the expression of cellular activating factors, western blotting was conducted using the anti-pERK (Santa Cruz Biotechnology, USA) and p38 (Santa Cruz Biotechnology, USA) antibodies.

It was verified that the treatment of cells with CG-Renuin or CG-Noverin increased the phosphorylation of ERK and P38 involved in cell proliferation, migration, and survival (FIGS. 3a and 3b).

Example 3: rhMMP2 Inhibition by CG-Renuin or CG-Noverin

After rhMMP2 was mixed with the peptides at different concentrations (0.1 ug/ml and 1 ug/ml), the incubation was conducted at room temperature for 1 hour. Then, in order to investigate the expression of rhMMP2 through gelatin zymography, protein electrophoresis (SDS-PAGE) was conducted using gelatin (2 mg/ml) as a substrate. After the electrophoresis, the gel was immersed in 2.5% Triton X-100 for 30 minutes, and then incubated in a buffer containing 50 mM Tris-HCl, 0.2 M NaCl, 5 mM $CaCl_2$, and 1% Triton X-100 at 37° C. for 24 hours. After the incubation, the gel was stained with Coo-massie Brilliant Blue R250 (Sigma), and de-stained with a solution containing 5% methanol, 7.5% acetic acid, and distilled water. In addition, the bands formed by gelatin hydrolysis were observed. The bands of 66-kDa were observed for active MMP-2 and the bands of 72 kDa were observed for pro-MMP-2.

It was verified through the gelatin zymography that MMP2 activity was directly inhibited by CG-Renuin and CG-Noverin (FIGS. 4a and 4b).

Example 4: rhMMP2 Inhibition by CG-Renuin or CG-Noverin in Fibroblast Cells

Fibroblast cells (NIH3T3) were seeded in a 24-well plate at a cell density of $3\times10^4$ cells/well. The next day, the cells were incubated in serum-less medium for 24 hours, and the expression and activation of MMP2 were induced by TNF-α. The cells were treated with CG-Renuin or CG-Noverin at different concentrations (10 ng/ml, 100 ng/ml, 1000 ng/ml), followed by incubation for 24 hours. The supernatant obtained from centrifugation at 14,000×g for 10 minutes was incubated, and then, in order to investigate the expression of MMP2 through gelatin zymography, protein electrophoresis (SDS-PAGE) was conducted using gelatin (2 mg/ml) as a substrate. After the electrophoresis, the gel was immersed in 2.5% Triton X-100 for 30 minutes, and then incubated in a buffer containing 50 mM Tris-HCl, 0.2 M NaCl, 5 mM $CaCl_2$, and 1% Triton X-100 at 37° C. for 24 hours. After the incubation, the gel was stained with Coo-massie Brilliant Blue R250 (Sigma), and de-stained with a solution containing 5% methanol, 7.5% acetic acid, and distilled water. In addition, the bands formed by gelatin hydrolysis were observed. The bands of 66-kDa were observed for active MMP-2 and the bands of 72 kDa were observed for pro-MMP-2.

It was verified from the observation results of MMP2 activity that MMP2 activity was inhibited by CG-Renuin and CG-Noverin (FIGS. 5a and 5b).

Example 5: Inhibition of Collagen Degradation by CG-Renuin or CG-Noverin

Human dermal fibroblast (HDF) cells ($3\times10^4$) were seeded in a 24-well plate. The next day, the cells were incubated in 5% serum medium for 42 hours, treated with MMP2 (20 ng/ml, SIGMA/USA) and CG-Noverin or CG-Renuin, respectively, and incubated for 6 hours. The supernatant obtained from centrifugation at 14,000×g for 10 minutes was analyzed using the pro-collagen type I kit (RnD system/USA).

Human dermal fibroblast (HDF) cells ($3\times10^4$) were seeded in a 24-well plate, and then the next day, the medium was exchanged with a 5% serum medium. The cells were treated with IGF-1 (100 ng/ml, Sigma/USA), followed by incubation for 44 hours, and then the cells were treated with MMP2 (20 ng/ml) and CG-Noverin or CG-Renuin, respectively, followed by incubation for 4 hours. The supernatant obtained from centrifugation at 14,000×g for 10 minutes was analyzed using the pro-collagen type I kit.

As a result of testing whether CG-Renuin and CG-Noverin have functions of inhibiting the collagen degradation induced by MMP2, it was verified that the MMP2 treatment increased the intracellular degradation of collagen when compared with a control group, and inhibited the induction of collagen degradation by co-treatment with CG-Renuin or CG-Noverin (FIGS. 6a-6b and 7a-7b).

Example 6: Inhibition of Melanosome Transfer by CG-Noverin and CG-Renuin

In order to observe melanosome transfer, phagocytosis assay was conducted using HaCaT keratinocytes. Bioparticles with a fluorescence substance attached thereto were used as a substance for phagocytosis. The cells were seeded in a 96-well tissue culture plate at $3\times10^3$ cells/well, incubated for 24 hours, and then incubated in a serum-free medium for 6 hours. Thereafter, for the induction of phagocytosis, the cells were treated with 1 μg/ml of trypsin, and then the cells were treated with 1 μg/ml of peptides for 48 hours. As a result, it was confirmed through a fluorescent microscope that the bioparticles were phagocytized into keratocytes. From the observation when the data with respect to a phagocytosis induction group, that is, a trypsin treatment group, were considered to be 100%, it was verified that phagocytosis was inhibited in the CG-Noverin treatment group and the CG-Renuin treatment group.

Example 7: Anti-Periodontal Function of CG-Noverin

Anti-Inflammatory Effect by Synthetic Peptides in Periodontitis Cells

In order to observe anti-inflammatory effects by the peptides synthesized in the synthesis example in periodontitis cells, a test was conducted using human periodontal ligament fibroblast cells (ATCC, USA) The human periodontal ligament fibroblast cells were seeded in a 6-well tissue culture plate at 5×10$^1$ cells/well for 24 hours. For the induction of inflammation in periodontal cells, the cells were treated with 10 ug/ml trypsin (Sigma, USA), and then the cells were treated with the peptides of the present invention at 1 ug/ml, followed by incubation for 4 hours. Then, mRNA was extracted from the cells incubated through the treatment with a control and an inducer, and an inducer and the peptides, followed by a reverse transcription polymerase chain reaction using primers of PAR-2 and IL-1β. Nucleotide sequences for respective primers used are shown in table 2.

TABLE 2

| | | |
|---|---|---|
| IL-1β | Forward | 5'-CCGTGGACCTTCCAGGATCA-3' |
| IL-1β | Reverse | 5'-GATCCACACTCTCCAGCTGC-3' |
| PAR2 | Forward | 5'-GGGTTTGCCAAGTAACGGC-3' |
| PAR2 | Reverse | 5'-GGGAACCAGATGACAGAGAGG-3' |

As can be seen from FIG. 9, when human periodontal ligament fibroblast cells were treated with trypsin to induce inflammation, the increased expressions of inflammatory cytokines, PAR-2 and IL-1β, were observed. In addition, the expressions of the two inflammatory cytokines were significantly inhibited by the simultaneous treatment of trypsin with the peptides of the present invention (FIG. 9).

Although the present invention has been described in detail with reference to the specific features, it will be apparent to those skilled in the art that this description is only for a certain embodiment and does not limit the scope of the present invention. Thus, the substantial scope of the present invention will be defined by the appended claims and equivalents thereof.

The invention claimed is:

1. A peptide having an activity to improve skin condition, the peptide consisting of the amino acid sequence of SEQ ID NO: 2, wherein (i) the C-terminal end of the peptide is modified by the presence of a hydroxyl group, an amino group, or an azide group, or (ii) the N-terminal end of the peptide comprises a protecting group.

2. The peptide of claim 1, wherein the peptide inhibits the activity of matrix metalloproteinase-2 (MMP2).

3. The peptide of claim 1, wherein the peptide inhibits collagen degradation.

4. The peptide of claim 1, wherein the peptide inhibits melanosome transfer.

5. The peptide of claim 1, wherein the improving of the skin condition is wrinkle relief, skin regeneration, skin elasticity improvement, skin aging inhibition, wound tissue regeneration, acne relief, skin regeneration or skin whitening.

6. The peptide of claim 1, wherein the C-terminal end of the peptide is modified by the presence of a hydroxyl group, an amino group, or an azide group, and the N-terminal end of the peptide comprises a protecting group.

7. The peptide of claim 1, wherein the protecting group is selected from the group consisting of: acetyl group, a fluorenyl methoxy carbonyl group, a formyl group, a palmitoyl group, a myristyl group, a stearyl group and polyethylene glycol (PEG).

* * * * *

SEQUENCE LISTING

```
<160> NUMBER OF SEQ ID NOS: 6

<210> SEQ ID NO 1
<211> LENGTH: 9
<212> TYPE: PRT
<213> ORGANISM: Artificial Sequence
<220> FEATURE:
<223> OTHER INFORMATION: synthetic construct

<400> SEQUENCE: 1

Cys Thr Lys Ile Tyr Asp Pro Val Cys
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic construct

<400> SEQUENCE: 2

Cys Pro Arg His Phe Asn Pro Val Cys
1               5

<210> SEQ ID NO 3
<211> LENGTH: 20
<212> TYPE: DNA
<213> ORGANISM: Artificial Sequence
<220> FEATURE:
<223> OTHER INFORMATION: synthetic construct

<400> SEQUENCE: 3
ccgtggacct tccaggatca                                              20

<210> SEQ ID NO 4
<211> LENGTH: 20
<212> TYPE: DNA
<213> ORGANISM: Artificial Sequence
<220> FEATURE:
<223> OTHER INFORMATION: synthetic construct

<400> SEQUENCE: 4
```

```
gatccacact ctccagctgc                                         20

<210> SEQ ID NO 5
<211> LENGTH: 18
<212> TYPE: DNA
<213> ORGANISM: Artificial Sequence
<220> FEATURE:
<223> OTHER INFORMATION: synthetic construct

<400> SEQUENCE: 5
gggtttgcca agtaacgg                                           18

<210> SEQ ID NO 6
<211> LENGTH: 21
<212> TYPE: DNA
<213> ORGANISM: Artificial Sequence
<220> FEATURE:
<223> OTHER INFORMATION: synthetic construct

<400> SEQUENCE: 6
gggaaccaga tgacagagag g                                       21
```